United States Patent [19]

Ericsson

[11] 4,286,730
[45] Sep. 1, 1981

[54] METHOD AND AN APPARATUS FOR APPLYING OBJECTS TO A SURFACE

[76] Inventor: Magnus Ericsson, 7 Pyramidvägen, Solna, Sweden, S-171 36

[21] Appl. No.: 97,831

[22] Filed: Nov. 27, 1979

[51] Int. Cl.³ .............................................. B65H 3/22
[52] U.S. Cl. .................................................... 221/215
[58] Field of Search .......................... 221/214, 215, 1; 271/18.3

[56] References Cited

U.S. PATENT DOCUMENTS

| | | | |
|---|---|---|---|
| 142,822 | 9/1873 | Thian | 271/18.3 |
| 217,244 | 7/1879 | Simon | 271/18.3 |
| 4,042,145 | 8/1977 | Ehrlich | 221/94 |

*Primary Examiner*—Stanley H. Tollberg
*Attorney, Agent, or Firm*—Burns, Doane, Swecker & Mathis

[57] ABSTRACT

The invention relates to a method for applying objects such as antibiotic disc to a surface (2), e.g. the surface of a culture medium, by impaling them on an axially movable needle (3), which applies the object to the surface, after which a member (4) presses the object against the surface. The needle and the member are thereafter returned to the relative starting position. Moreover, the invention concerns a device for applying objects (1), such as an antibiotic disc to a surface (2), such as the surface of a culture medium, which device comprises at least one axially movable needle (3), a feeding surface (5), at least one hole (6) located in the feeding direction and at least one member (4) arranged so that it can press the object against the surface (2).

7 Claims, 8 Drawing Figures

METHOD AND AN APPARATUS FOR APPLYING OBJECTS TO A SURFACE

The present invention relates to a method and an apparatus for applying objects to a receiving surface and more specifically for applying antibiotic discs to an agar surface.

Several devices for applying antibiotic discs to an agar surface are known priorly. Most of these devices are equipped with a plurality of disc magazines from which antibiotic discs are fed by means of a reed-like member. For the application of the discs to the agar surface there are essentially two different methods in use.

According to one method (disclosed for example in Swedish Patent Specification 381103 and U.S. Pat. No. 3,934,753 the respective discs are allowed to drop freely through tubes, tapering or not, down onto the agar surface. The second method, as disclosed in Swedish Patent Specification 403520 and U.S. Pat. Nos. 3,836,047 and 4,042,145, employs a mechanism by which the antibiotic discs are pushed through the respective tubes down onto the agar surface.

Both methods thus employ tubes through which the antibiotic discs pass. These tubes terminate close to the agar surface. In order that the tubes shall not touch the agar surface, which might result in contamination by substances being transferred by the end faces of the tubes from one agar surface portion to another, these end faces are spaced some small distance above the rim of the Petri dish holding the agar substance, to eliminate the influence of different heights of agar layers and rim heights. Since a too great distance between the tube and the agar surface may cause a less than accurate positioning of the discs on the agar surface, the spacing must be kept as small as compatible with avoiding the risk of contamination. This will necessitate some free fall of the discs whereby the latter may become positioned edgewise and may also "float" away.

When employing these known methods the antibiotic discs have also to be pressed down manually after the application so as to lie close to the agar surface.

It is an object of the invention, therefore, to provide an improved method and apparatus for applying objects such as antibiotic discs to a receiving surface such as an agar surface.

According to the invention a method for applying objects such as antibiotic discs to a surface is characterized by the steps of moving a needle from a starting position, piercing the object by the needle, applying the object to the surface by means of the needle, pressing the object against the surface by a retaining means separate from the needle and returning the needle and the retaining means to their respective starting positions in that order.

In an apparatus according to the invention for applying objects such as antibiotic discs to a surface and having supply means for the objects and means for feeding the objects from the supply means, the improvement comprises the provision of at least one intermediate surface having holes therein, at least one pointed needle movable axially from a starting position and operable to pierce by its point an object lying on the intermediate surface and to transport said object down onto the receiving surface, at least one hole disposed in the direction of travel and coaxially with the direction of movement of the needle and the object, and at least one member being movable relative to the needle from a starting position to a position wherein it presses the object against the receiving surface.

The invention will be described hereinafter by way of example, reference being had to the drawings.

In the drawings.

The parts designated by numerals in FIGS. 1 to 5 have been allotted like reference numbers in FIGS. 6 to 8. The arrows in FIGS. 1 to 5 indicate the directions of motion of various parts.

Figure 1:
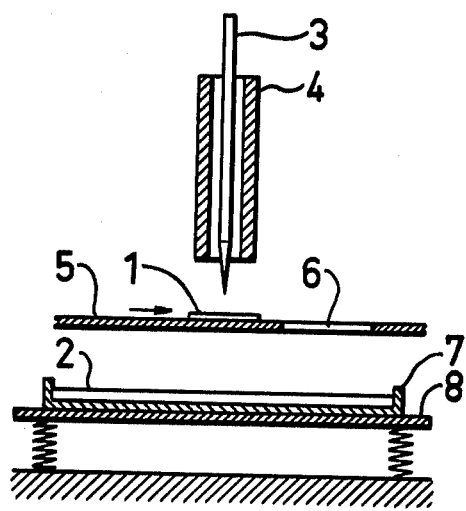
FIGS. 1 to 4 illustrate the cycle of operation of an apparatus carrying out the method according to the invention.
Figure 2:
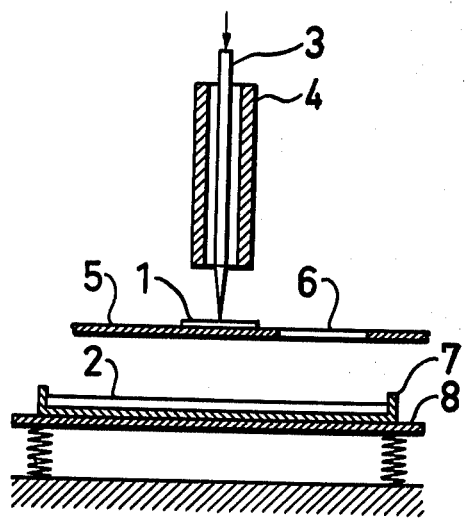

With reference to FIGS. 1 to 5, objects 1 such as antibiotic discs are stored in a supply magazine (not illustrated) and are fed from there by means of, for example, a reed-like feed member that conveys the object 1 from the magazine to an intermediate surface 5. This surface 5 conveys the object 1 in a horizontal plane to a position aligned with and underneath a pointed needle 3 and a member 4, such as a hollow sleeve concentrically surrounding the needle, said member and said needle being operable to move axially independently of each other. This relative position of the object 1, needle 3 and member 4 is illustrated in FIG. 1. The member 4, in another embodiment, may be disposed below the surface 5, for example in the shape of a claw or hook.

Figure 3:
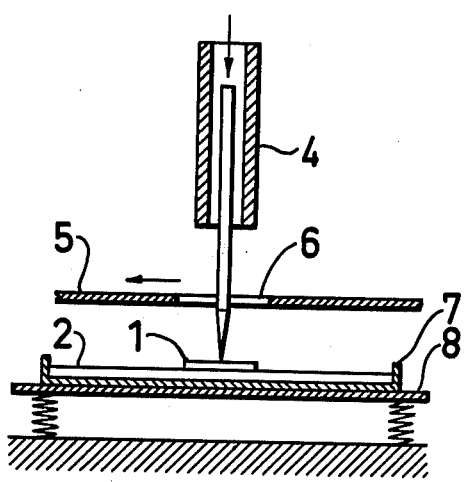
Figure 4:
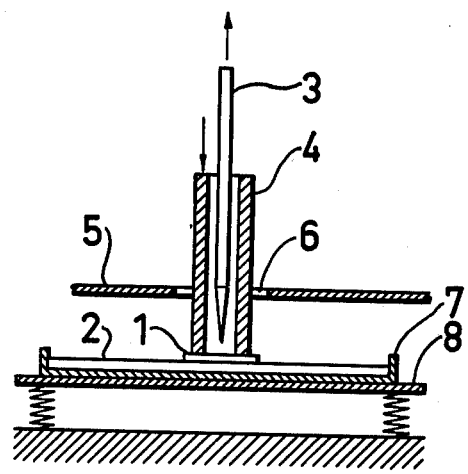

The needle 3 is advanced to pierce the object 1 (FIG. 2), and the intermediate surface 5 is returned to its initial position, whereby a hole 6 through the surface 5 and located in the direction of feed will become aligned with the path of travel of needle 3 and member 4. Subsequently the object 1, pierced on the needle 3 is moved downwards through the hole 6 and towards a receiving surface 2 such as the surface of an agar layer in a Petri dish 7 supported by a base member 8 (FIG. 3). The member 4 is moved downwards thereafter, so as to press the object 1 against the surface 2, and finally the needle 3 and the member 4, in that order, are returned to their respective starting positions (FIG. 4).

Figure 5:
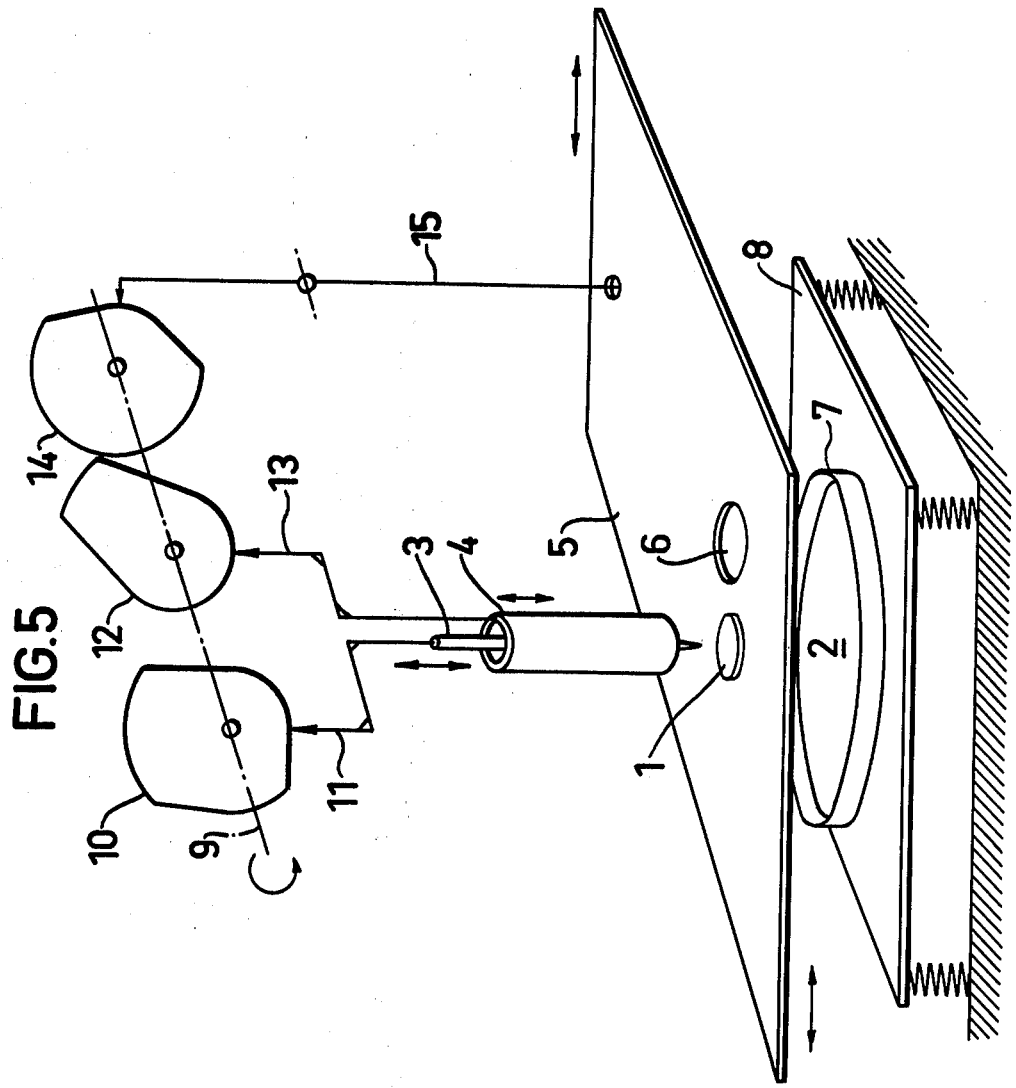
FIG. 5 illustrates diagrammatically a drive mechanism.

FIG. 5 illustrates diagrammatically a drive mechanism (upper portion of figure) that imparts the desired motion sequence to the needle 3, member 4 and intermediate surface 5. The drive mechanism comprises a drive shaft 9 on which there is provided first, second and third cams 10,12 and 14, respectively. On rotation of shaft 9 the cams command the motion of the needle 3, the member 4 and the surface 5 via a system of transmitting members 11,13 and a rocking lever 15.

Figure 6:
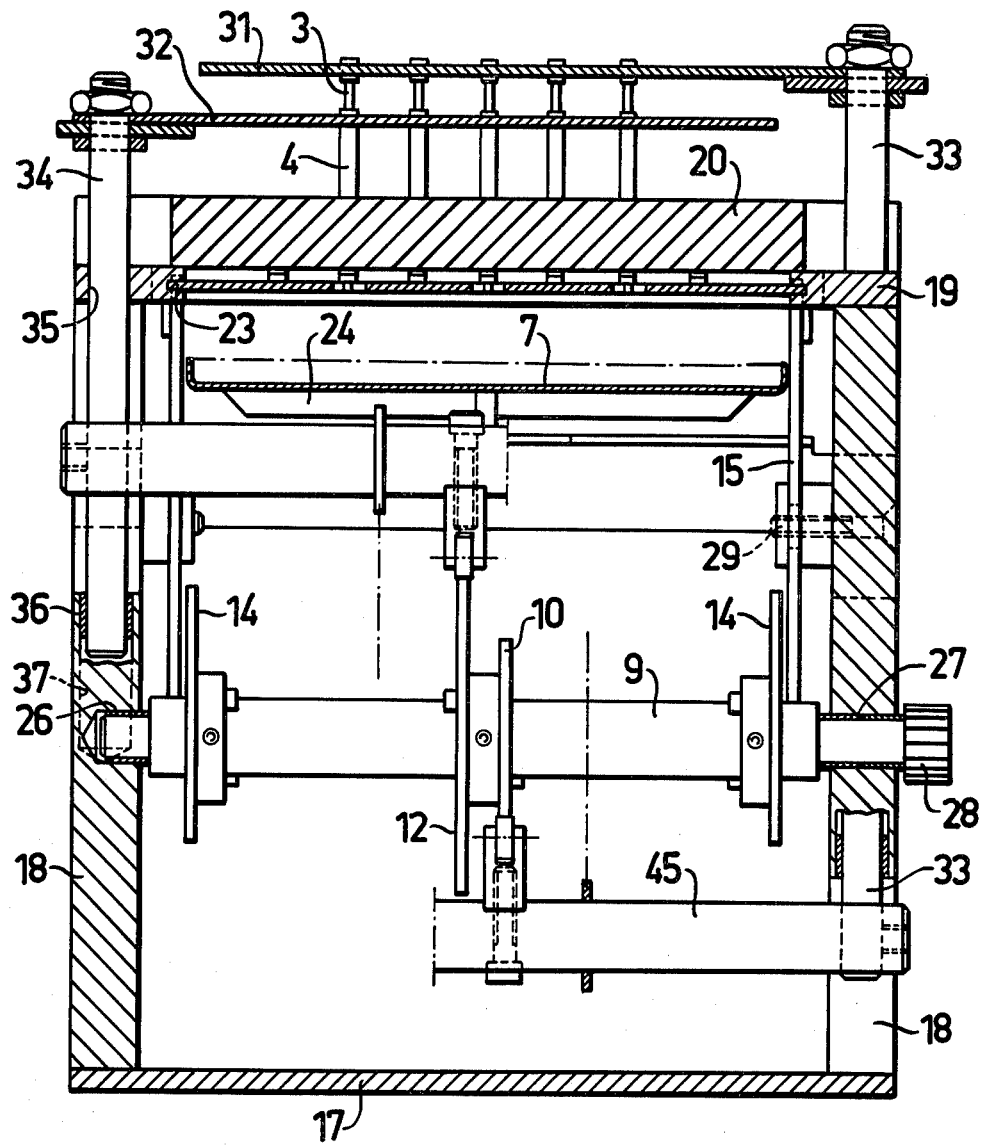
FIG. 6 is a sectional view along line VI—VI in FIG. 8 of an apparatus according to the invention.
Figure 7:
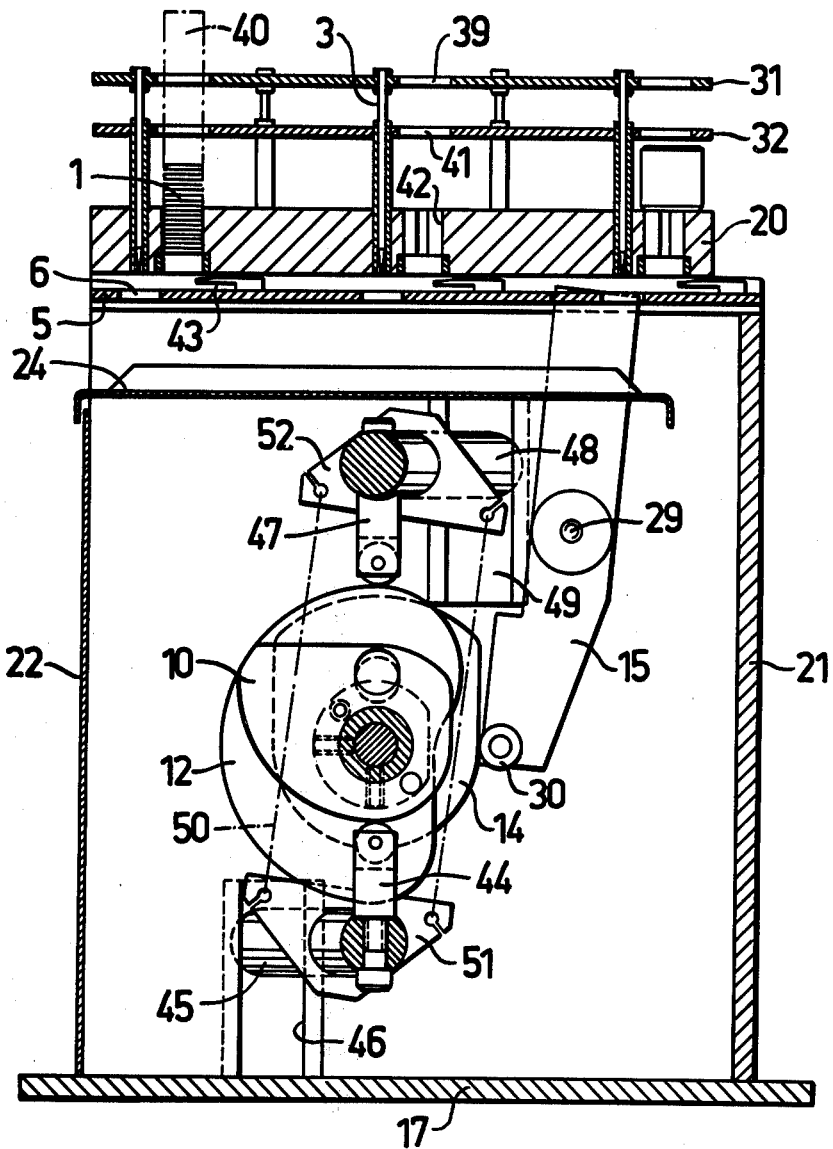
FIG. 7 is a sectional view along line VII—VII in FIG. 8.

In practice, the method and apparatus will make the simultaneous handling of several objects possible by the provision of a plurality of needles 3, members 4 and holes 6 in the intermediate surface 5, the drive mechanism being designed accordingly. An embodiment of an apparatus for applying several objects at a time to a receiving surface will now be described by way of example, reference being had to FIGS. 6 to 8.

To a bottom plate 17 two vertical parallel side plates 18 are fixed. On top of each side plate 18 a straight bar 19 is rigidly mounted. A top plate 20 is superposed on bars 19 and interconnects side plates 18. End walls or plates 21,22 are also provided. The parts now described form a rigid, box-like structure.

In the opposite faces of the bars 19 grooves 23 are machined and form guideways for a sliding plate 5 which provides the intermediate surface previously described. The plate 5 has a plurality of spaced holes 6 therein for passing antibiotic discs pierced by needles 3 through plate 5 downwards onto the surface of an agar layer held in a Petri dish 7. This dish 7 stands on a horizontal plate member 24 supported by the box structure.

A drive shaft 9 is journalled in bearings 26,27 in the side plates 18. The shaft extends beyond one side plate, and its projecting end carries a drive gear 28 for engagement with a drive motor (not illustrated). Instead of gear 28 a hand crank can be provided for rotating shaft 9 manually.

The drive shaft 9 carries close to each side plate 18 a cam 14, corresponding to the cam 14 illustrated in FIG. 5. The duplication of the cam 14 serves for imparting a balanced drive to plate 5 by means of a lever 15 at each side supported by pivot studs 29 from the side plates 18. A cam follower 30 is mounted at the lowermost part of each lever 15. The upper ends of the levers 15 engage plate 5 drivingly, near two transversely opposite corners. On rotation of shaft 9, a reciprocating motion is imparted to plate 5. A non-illustrated coupling of a known or suitable kind interrupts the rotation of the shaft after each full revolution.

Some distance above the relatively thick, fixed top plate 20 two spaced thinner plates 31 and 32 are provided. Thse plates 31,32 are reciprocable up and down by being each supported by pairs of diametrically disposed vertical rods 33,34, respectively, guided in holes 35 through the bars 19 as well as by bushes 36 inserted into bores 37 in the recessed sideplates 18.

Figure 8:
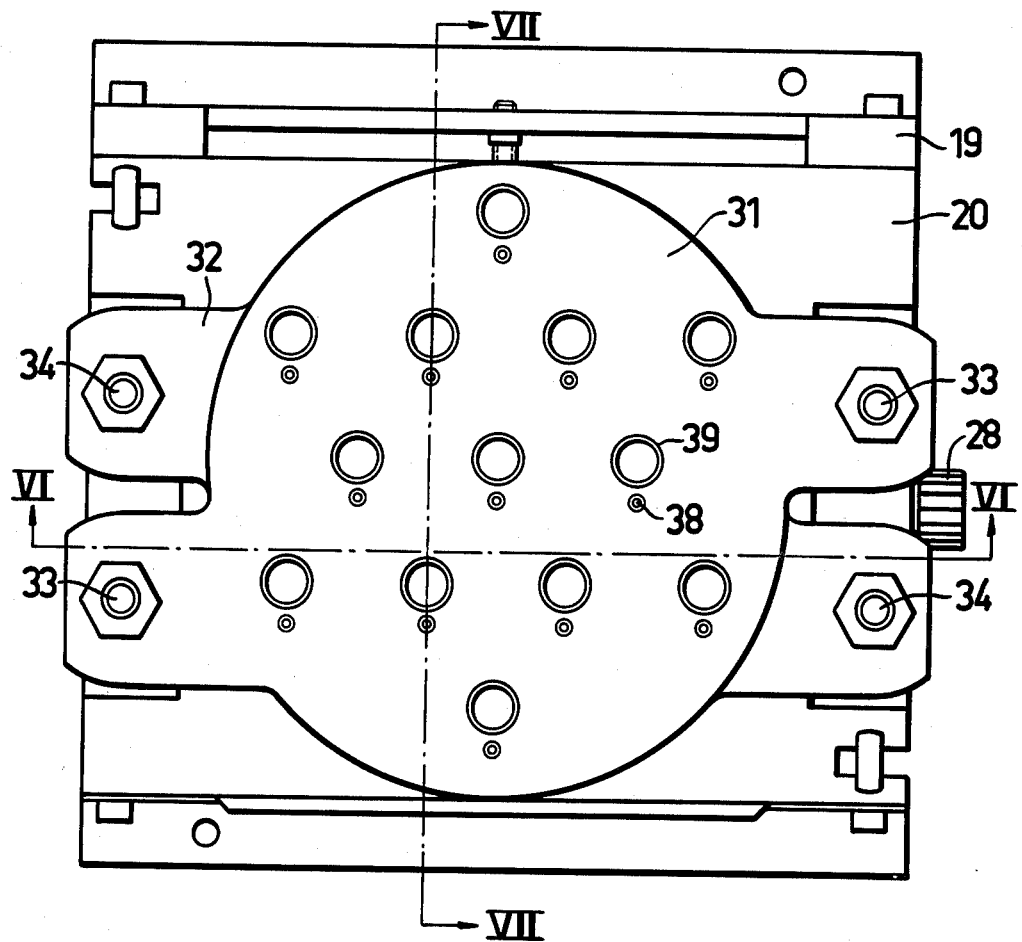
FIG. 8 is a top plan view.

Both plates 31,32 are formed with a plurality of holes in a pattern corresponding to the holes 6 in plate 5. FIG. 8 illustrates the arrangement of holes in the topmost plate 31. The smaller circles 38 represent holes with the upper end portions of the needles 3 secured therein, whereas the larger circles 39 represent additional holes for inserting magazines or cartridges 40 each holding a supply of antibiotic discs. The lower plate 32 is formed with similar holes. The smaller of these holes are larger than the holes 38 and provide fastening for sleeve members 4 surrounding the needles coaxially, whereas the larger holes 41 correspond to holes 39 in the topmost plate.

In the fixed plate 20 there are guide bores for the sleeves 4 as well as sockets 42 for the magazines 40. The latter can be of a type known in itself, formed substantially as a small tube and shaped in the bottom end for engagement of the nethermost antibiotic disc by hook- or reed-shaped members 43 disposed on the upper face of plate 5.

For the reciprocating motion of the plates 31 and 32 there are provided cams 10 and 12, respectively, on drive shaft 9. The cam 10 is engaged by a cam follower 44 secured to an obliquely disposed transverse rod 45 the end portions of which are guided by the lateral sides of recesses 46 in the side plates 18. The bottom ends of the vertical rods 33 carrying plate 31 are secured to the transverse rod 45. On rotation of shaft 9 the cam 10 will impart a reciprocating up and down motion to plate 31.

The cam 12 is engaged by a cam follower 47 secured to an oppositely obliquely disposed transverse rod 48 in the upper part of the fixed structure having its end portions guided in recesses 49 in the side plates 18. Rod 48 has its end portions secured to rods 34 carrying plate 32, and rotation of shaft 9 will impart to the plate the desired reciprocating motion, the cams 10,12 and 14 being shaped in such way and mounted in such relationship that the operation sequence described with reference to FIGS. 1 to 5 will be performed. Since the cams are single-acting the necessary biassing forces are provided by tension springs such as 50 which are suspended between yoke members 51,52 mounted on the rods 45,48, respectively.

What I claim is:

1. A method for applying an object, such as an antibiotic disc, to a receiving surface, such as the surface of a culture medium, characterized by the steps of supporting the object on an intermediate surface with at least one hole located therein, moving a needle axially from a starting position, piercing the object by the needle, positioning the intermediate surface such that a hole is aligned with the needle, passing the object through the hole in the intermediate surface, applying the object to the receiving surface by means of the needle, pressing the object against the receiving surface by a member separate from the needle, and returning the needle and said member to their respective starting positions in that order.

2. A method according to claim 1, characterized by feeding the object from a supply source before piercing it by the needle.

3. A method according to claim 1, characterized by the pressing down of the object against the receiving surface by means of said member along an area surrounding the needle and substantially annular-shaped.

4. An apparatus for applying objects, such as an antibiotic disc, to a receiving surface, such as the surface of a culture medium, said apparatus comprising supply means holding the objects and means for feeding out the objects from said supply means, characterized by the provision of at least one intermediate surface formed with holes therein, by the provision of at least one pointed needle capable of axial travel from a starting position into a position wherein it will pierce by its point an object lying on said intermediate surface, said intermediate surface being operable to bring one of said holes in alignment with said needle, said needle being further operable to convey said object through said hole down onto the receiving surface, and further by the provision of object retaining means operable to perform a motion cycle independent of that of the needle whereby to keep the object affixed to the receiving surface temporarily during withdrawal of the needle.

5. An apparatus according to claim 4, characterized in that said object retaining means is a hollow sleeve surrounding the needle and substantially coaxial therewith.

6. An apparatus according to claim 5, characterized by a plurality of spaced pointed needles arranged in a two-dimensional pattern, a like plurality of sleeve members disposed coaxially around said needles, a first supporting plate member carrying said needles, a second supporting plate member spaced below said first plate member and carrying said sleeve members, there being aligned holes in said plate members, a guide plate spaced below said second plate member and having guide bores therein for said sleeve members and further having socket means aligned with said holes in said first and second plate members, a third plate member spaced below said guide plate and having holes therein, said third plate member being operable to travel reciprocatingly between a first position wherein surface portions thereof are in alignment with magazines holding a supply of antibiotic discs and inserted in said holes in said first and second plates and into said sockets, and wherein said holes are aligned with said needles and sleeves, and a second position wherein the said surface portions with antibiotic discs lying thereon are in alignment with said needles, means on said third plate member for feeding out an antibiotic disc at a time from each magazine, supporting means spaced below said third plate member for a receptacle holding a medium presenting said receiving surface, and a drive mechanism for imparting a motion sequence to said first, second and third plate members such that antibiotic discs are fed onto said third plate member during travel thereof into an end position underneath said needles, that the needles are moved down to pierce said discs by said first plate member being lowered, that said third plate member is reciprocated to bring its holes into alignment with the needles, that said first plate member is lowered further to apply the antibiotic discs to the receiving surface, that the second plate member is lowered to bring said sleeves to press down the antibiotic discs against the receiving surface and to stay in this position while said first plate member is raised to remove said needles from the discs and that the second plate member is raised subsequently to resume together with the first and third plate members its initial position.

7. An apparatus according to claim 6, characterized in that said drive mechanism comprises a drive shaft having cams for imparting a motion sequence to the said first, second and third plate members, said drive shaft being journalled in a stationary structure supporting and guiding said plate members for motion relative thereto.

* * * * *